US006482820B2

(12) United States Patent
Wilkins et al.

(10) Patent No.: US 6,482,820 B2
(45) Date of Patent: Nov. 19, 2002

(54) PHARMACEUTICAL COMPOSITIONS AND METHOD FOR THE INHIBITION AND TREATMENT OF SECONDARY HYPERTENSION

(75) Inventors: Martin R. Wilkins, Buckinghamshire (GB); Dirk Thormaehlen, Rheden (DE); Harald Waldeck, Isernhagen (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 0 days.

(21) Appl. No.: 09/930,186

(22) Filed: Aug. 16, 2001

(65) Prior Publication Data

US 2002/0052361 A1 May 2, 2002

Related U.S. Application Data

(63) Continuation of application No. PCT/EP00/01068, filed on Feb. 10, 2000.

(30) Foreign Application Priority Data

Feb. 16, 1999 (DE) .......................................... 199 06 310

(51) Int. Cl.$^7$ ............................................... A61K 31/55
(52) U.S. Cl. ....................................................... 514/213
(58) Field of Search .......................................... 514/213

(56) References Cited

U.S. PATENT DOCUMENTS

| 4,749,688 A | 6/1988 | Haslanger ..................... 514/19 |
| 5,362,727 A | 11/1994 | Robl .......................... 514/214 |
| 5,677,297 A | 10/1997 | Waldeck et al. ............ 514/211 |

FOREIGN PATENT DOCUMENTS

| DE | 19510566 | 9/1996 |
| DE | 19638020 | 3/1998 |
| GB | 2207351 | 2/1989 |

*Primary Examiner*—Phyllis G. Spivack
(74) *Attorney, Agent, or Firm*—Crowell & Moring LLP

(57) ABSTRACT

The present invention relates to the use of benzazepine-N-acetic acid derivatives which contain an oxo-group in the α-position to the nitrogen atom and are substituted in position 3 by a 1-(carboxyalkyl)cyclo-entylcarbonylamino radical, and their salts and biolabile esters for the treatment of hypertension, particularly for the treatment of certain forms of secondary hypertension, in larger mammals and particularly humans, and for the production of pharmaceutical compositions suitable for this treatment. The cause of the hypertension to be treated may have a wide variety of origins. The invention particularly relates to the treatment of those forms of secondary hypertension which may occur as a result of various non-cardiac diseases.

10 Claims, No Drawings

PHARMACEUTICAL COMPOSITIONS AND METHOD FOR THE INHIBITION AND TREATMENT OF SECONDARY HYPERTENSION

CROSS REFERENCE TO RELATED APPLICATIONS

This application is a continuation of International Patent Application No. PCT/EP00/01068, filed Feb. 10, 2000, designating the Unites States of America, the entire text of which is incorporated herein by reference. Convention priority is also claimed based on Federal Republic of Germany patent application no. DE 199 06 310.9, filed Feb. 16, 1999.

BACKGROUND OF THE INVENTION

The present invention relates to the use of benzazepine-N-acetic acid derivatives which contain an oxo-group in the α-position to the nitrogen atom and are substituted in position 3 by a 1-(carboxyalkyl)cyclo-pentylcarbonylamino radical, and their salts and biolabile esters for the treatment of hypertension, particularly of certain forms of secondary hypertension, in larger mammals and particularly humans, and for the production of pharmaceutical compositions suitable for this treatment. The cause of the hypertension to be treated can have a wide variety of origins. In particular, the invention relates to the treatment of those forms of secondary hypertension which may occur as a result of various non-cardiac diseases.

Benzazepine-N-acetic acid derivatives which contain an oxo group in α-position to the nitrogen atom and are substituted in position 3 by a 1-(carboxyalkyl)cyclopentyl-carbonylamino radical, and their salts and biolabile esters fall under the scope of protection of the benzazepine, benzoxazepine and benzothiazepine-N-acetic acid derivatives which contain an oxo group in the α-position to the nitrogen atom and are substituted in position 3 by a 1-(carboxyalkyl)cyclopentyl-carbonylamino radical and have NEP-inhibitory effects on the heart, as described in Waldeck et al., U.S. Pat. No. 5,677,297 (=DE 195 10 566). The benzazepine-N-acetic acid compounds used in the present invention can be produced by the methods described in said U.S. Pat. No. 5,677,297.

SUMMARY OF THE INVENTION

The object of the invention is to develop a novel method for inhibiting hypertension.

In particular, it is an object of the invention to provide a method of treating certain forms of secondary hypertension.

It is especially an object of the invention to develop a method for the treatment of those forms of secondary hypertension which may occur as a result of various non-cardiac diseases.

These and other objects have been achieved in accordance with the present invention by providing a method of inhibiting hypertension in a mammal, said method comprising administering to said mammal an effective hypertension inhibiting amount of a compound corresponding to formula I:

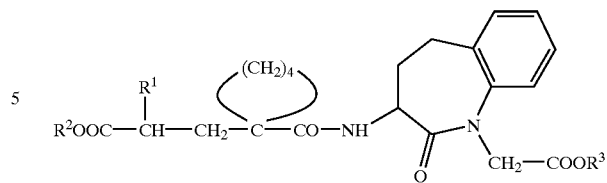

wherein
$R^1$ stands for a phenyl-lower-alkyl group which can optionally be substituted in the phenyl ring by lower alkyl, lower alkoxy or halogen, or for a naphthyl-lower-alkyl group,
$R^2$ means hydrogen or a group forming a biolabile ester and
$R^3$ means hydrogen or a group forming a biolabile group, or a physiologically acceptable salt of an acid of formula I.

DETAILED DESCRIPTION OF PREFERRED EMBODIMENTS

According to the invention compounds of the general formula I

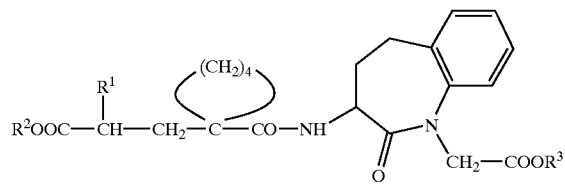

wherein
$R^1$ stands for a phenyl-lower-alkyl group which can be optionally substituted in the phenyl ring by lower alkyl, lower alkoxy or halogen, or for a naphthyl-lower-alkyl group,
$R^2$ means hydrogen or a group forming a biolabile ester and
$R^3$ means hydrogen or a group forming a biolabile ester and physiologically acceptable salts of the acids of formula I are used for the production of pharmaceutical compositions for the treatment of hypertension, particularly for the treatment of certain forms of secondary hypertension, in larger mammals and humans.

Insofar as the substituents in the compounds of formula I are or contain lower alkyl or alkoxy groups, these can be straight-chain or branched and contain, in particular, 1 to 4, preferably 1 to 2, carbon atoms and are preferably methyl or methoxy. Where the substituents contain halogen, particularly suitable are fluorine, chlorine or bromine, preferably fluorine or chlorine.

In the radical $R^1$, the lower alkylene chain can contain 1 to 4, preferably 1 to 2, carbon atoms. $R^1$ in particular is an optionally substituted phenethyl group which can optionally be substituted one or more times by halogen, lower alkoxy or lower alkyl, or is a naphthyl-ethyl group.

The compounds of formula I are optionally esterified dicarboxylic acid derivatives. Depending on the mode of administration, biolabile monoesters, particularly compounds in which $R^2$ is a group forming a biolabile ester and $R^3$ is hydrogen, or dicarboxylic acids are preferred, the latter being particularly suitable for i.v. administration.

Suitable $R^2$ and $R^3$ groups forming biolabile esters include lower alkyl groups, phenyl or phenyl-lower-alkyl groups which are optionally substituted in the phenyl ring by lower alkyl or by a lower alkylene chain bonded to two adjacent carbon atoms, dioxolanylmethyl groups which are optionally substituted in the dioxolane ring by lower alkyl, or $C_2$–$C_6$-alkanoyloxymethyl groups optionally substituted on the oxymethyl group by lower alkyl. Where the $R^2$ or $R^3$ group forming a biolabile ester is lower alkyl, this can be a preferably unbranched alkyl group with 1 to 4, preferably 2, carbon atoms. Where the group forming a biolabile ester is an optionally substituted phenyl-lower-alkyl group, its alkylene chain can contain 1 to 3, preferably 1, carbon atom. Where the phenyl ring is substituted by a lower alkylene chain, this can contain 3 to 4, particularly 3, carbon atoms. Phenyl, benzyl or indanyl are particularly suitable as phenyl-containing substituents $R^2$ and/or $R^3$. Where $R^2$ and/or $R^3$ are an optionally substituted alkanoyloxymethyl group, their alkanoyloxy group can contain 2 to 6, preferably 3 to 5, carbon atoms and is preferably branched and can be, for example, a pivaloyloxymethyl radical tert-butylcarbonyl-oxymethyl radical).

Suitable physiologically acceptable salts of dicarboxylic acids or monoesters of formula I include their alkali metal, alkaline earth metal or ammonium salts, for example sodium or calcium salts or salts with physiologically acceptable, pharmacologically neutral organic amines such as, for example, diethylamine or tert-butylamine.

The compounds of formula I contain two asymmetric or chiral carbon atoms, namely the carbon atom which is in position 3 of the ring framework and carries the amide side-chain, and the carbon atom of the amide side-chain which carries the $R^1$ group. The compounds can therefore exist in several optically active stereoisomeric forms or as a racemate. According to the present invention both the racemic mixtures and the isomerically pure compounds of formula I may be used.

It has now surprisingly been found that the group of compounds of formula I used according to the invention—particularly with regard to certain secondary forms of hypertension—have a blood pressure-lowering effect in humans and larger mammals. The compounds of formula I and their physiologically acceptable salts of the acids and their biolabile esters are thus suitable for the treatment of hypertension, particularly for the treatment of certain forms of secondary hypertension in which the hypertension to be treated may have a wide variety of origins.

The compounds of formula I, including their salts of acids and their biolabile esters, are advantageously suitable for the treatment of those forms of secondary hypertension which may occur as a result of various non-cardiac diseases.

As used herein, the term "hypertension" (high blood pressure) means an increase in blood pressure beyond the normal level, which mainly becomes evident as arterial hypertension. Bearing in mind the aetiology of the high blood pressure, a distinction is made between two basic forms, namely essential or primary hypertension on the one hand and the forms of secondary hypertension on the other. As a rule, essential hypertension is caused by increased flow resistance resulting from at first purely functional, later organic narrowing of the arterial circulation. Secondary or symptomatic hypertension, conversely, is an organ-related hypertension, i.e. provoked by the disease of an organ, which may take the form of endocrine, renal, pulmonary or cardiovascular hypertension, for example. The diseases causally responsible for secondary hypertension can be of a diverse nature, e.g. chronic obstructive airways diseases or chronic asthma. Normal circulation of the blood in the lungs of an adult person takes place at lower pressure and with low resistance. However, pre-existing chronic hypoxia, such as can occur, for example, in chronic obstructive airways diseases, leads to pulmonary arterial hypertension and to the remodelling of pulmonary arterioles (increased growth of vascular muscle cells) and of the right ventricle (increased growth of myocardial cells).

The compounds of formula I, including their salts of acids and their biolabile esters, can be used particularly advantageously for the treatment of pulmonary hypertension, particularly if it is non-cardiac in origin. Pulmonary hypertension can exist as a primary form (with unknown cause) or as secondary pulmonary hypertension and can be treated with the compounds of formula I and their physiologically acceptable salts of acids and their biolabile esters.

As used herein, (Secondary) pulmonary hypertension (high pressure in the pulmonary circulation) means a consistent increase in mean pressure in the pulmonary arterial system to levels >22 mmHg at rest. This mean pressure increase can arise as a result, for example, of heart-related congestion in the pulmonary circulation (e.g. mitral valve defects, left heart failure), vasospasm before the capillary region (e.g. as a result of hypoxia at high altitude, obstructive pulmonary emphysema, following surgery that reduces lung size), secondary vascular atrophy (in pulmonary fibrosis, destructive pulmonary emphysema), excessive perfusion, i.e. hypercirculation in the pulmonary circulation with subsequent lumen-narrowing vascular disease (e.g. in heart defects with a large left-right shunt), recurrent pulmonary embolisms, as a side-effect of taking certain appetite suppressants (e.g. aminorex) or as a result of primary pulmonary vasoconstriction (=idiopathic=primary vascular pulmonary hypertension).

For treatment of hypertension according to the invention, the compounds of formula I and their physiologically acceptable salts of acids and their biolabile esters in conventional pharmaceutical compositions, can be administered by the oral, intravenous or transdermal route.

The compounds of formula I and their physiologically acceptable salts of acids and their biolabile esters in an effective blood pressure-lowering amount, together with conventional pharmaceutical adjuvants and/or carriers, can be contained in solid or liquid pharmaceutical compositions. Examples of solid preparations include orally administered preparations such as tablets, coated tablets, capsules, powder or granules, or also suppositories or patches (transdermal treatment systems). These solid preparations may contain pharmaceutically conventional inorganic and/or organic carriers, e.g. lactose, talc or starch, as well as pharmaceutically conventional adjuvants, for example lubricants or tablet disintegrants. Liquid preparations such as solutions, suspensions or emulsions of the active ingredients may contain the conventional diluents such as water, oils and/or suspending agents such as polyethylene glycols and similar agents. Other adjuvants may also be added, such as, for example, preservatives, taste corrigents and similar additives.

The active ingredients can be mixed and formulated with the pharmaceutical adjuvants and/or carriers in a known manner. For the preparation of solid pharmaceutical forms, the active ingredients can, for example, be mixed with the adjuvants and/or carriers in a conventional manner and granulated wet or dry. The granules or powder can be filled directly into capsules or compressed to form tablet cores in a conventional manner. These can optionally be coated in a known manner. Liquid compositions can be obtained in the form of solutions or suspensions by dissolving or dispersing the active ingredients and optionally other adjuvants in a suitable liquid carrier.

The blood pressure-lowering effect of the compounds of formula I according to the invention can be demonstrated in pharmacological tests in vivo on chronically hypoxic rats by measuring the effect of the substance in relation to pharmacological indicators suitable for that purpose, e.g. by measuring pulmonary artery pressure and right ventricular weight, and by investigating the pulmonary vessel remodelling in hypoxic rats.

DESCRIPTION OF THE TEST METHODS AND RESULTS

The test substance employed was (3S,2R')-3-[1-(2'-(carboxy-4'-phenylbutyl)cyclopentane-1-carbonylamino]-2, 3,4,5-tetrahydro-2-oxo-1H-1-benzazepine-1-acetic acid, which is representative of the substances of formula I which can be used in the invention. The dose of the substance administered was 40 mg/kg per day (sufficient to suppress the pressure feedback on big endothelin).

The test animals used were Sprague-Dawley rats (260 to 310 g; n=6 to 10 per test group). In order to produce pulmonary hypertension, the animals were exposed to acutely hypoxic conditions in a pressure chamber. For comparison, one control group was kept under normal air and another control group under hypoxic conditions.

Test Procedure:

The animals were treated with the active substance or a vehicle by means of osmotic mini-pumps. The osmotic mini-pumps had been implanted intraperitoneally in the animals before they were kept in a pressure chamber 24 h later for a period of two weeks. There the animals were kept at normal pressure either under hypoxic conditions (10% $O_2$) or in normal air. After two weeks the animals were prepared for the haemodynamic tests and the measurements were carried out.

Hemodynamic Tests:

The animals were anaesthetised, then a ready-made cannula was inserted into the pulmonary artery in a conventional manner via the right jugular vein, atrium and ventricle. A catheter was inserted into the left jugular vein in order to allow intravenous administration of active substances. The left carotid artery was also fitted with a cannula for the purpose of measuring systemic blood pressure. Once the animals were conscious, pulmonary artery pressure (PAP) was recorded. The rats were then exposed to hypoxic conditions (10% $O_2$) again for 10 minutes in a mini-chamber and the increase in pulmonary artery pressure was measured and also recorded. The effects of the test substance on PAP under normotoxic and hypoxic conditions are presented in Table 1 in comparison with the control tests. The given data are means ± standard deviations and were statistically analysed by means of ANOVA.

Measurement of the Antihypertrophic Effect:

After completion of the haemodynamic tests, the animals were sacrificed and their hearts were dissected out. The weights of the right and left ventricles were determined and calculated in relation to bodyweight. The effects of the test substance on the heart weights under normotoxic and hypoxic conditions are presented in Table 1 in comparison with the control tests. The given data are means ± standard deviations and were statistically analysed by means of ANOVA.

Investigation of the Effect on Pulmonary Artery Remodelling:

After the rats had been sacrificed, the lungs as well as the hearts were isolated. The lungs underwent histological examination, i.e. the degree of muscularisation of the distal pulmonary vessels was determined after "van Gieson" staining, by microscopy at 400× magnification. The effects of the test substance on pulmonary artery remodelling (i.e. on muscularisation of the distal pulmonary vessels) during two weeks' hypoxia are presented in Table 2 in comparison with the hypoxic control tests. The given data are means±standard deviations and were statistically analysed by means of ANOVA.

Results:

Given the described test method, treatment with the test substance in hypoxic animals led to a statistically significant decrease in pulmonary artery pressure (PAP), in comparison with the hypoxic control animals (Table 1) At the same time, normal systemic blood pressure was unaffected, i.e. no hypotensive properties were observed. This is particularly advantageous because it means there is no risk of a blood pressure decrease to below normal levels in normotensive persons with pulmonary hypertension.

TABLE 1

Effects of the substance used according to the invention (40 mg/kg/day for 14 days) on pulmonary artery pressure and the right and left heart weights of rats under 14-day normoxic and hypoxic conditions.

| | Normoxia | | Hypoxia | |
| --- | --- | --- | --- | --- |
| Parameter | Control n = 9 | Test substance n = 8 | Control n = 10 | Test substance n = 9 |
| PAP (mmHg) | 19.9 ± 2 | 22.2 ± 1 | 42.9 ± 1.6* | 33.2 ± 1.2*# |
| RtHWt (mg) | 178 ± 10 | 171 ± 10 | 269 ± 45* | 242 ± 6.4*# |
| Rt/LtHWt (mg/mg) | 0.25 ± 0.01 | 0.25 ± 0.01 | 0.45 ± 0.01* | 0.40 ± 0.02* |
| RtHWt/ BW (mg/g) | 0.54 ± 0.02 | 0.56 ± 0.03 | 0.94 ± 0.02* | 0.87 ± 0.03* |

Key to the table:
* = significantly different in comparison with normoxic control tests ($p < 0.05$)
# = significantly different in comparison with hypoxic control tests ($p < 0.05$)
PAP = pulmonary artery pressure
RtHWt = right ventricular weight (mg)
Rt/LtHWt = ratio of right to left ventricular weight
RtHWt/BW = ratio of right ventricular weight to body weight.

The decrease in pulmonary artery pressure by the test substance led to a statistically significant reduction of the right heart weight of the rats (antihypertrophic effect) in comparison with hypoxic control tests (Table 1). A tendency towards a reduction in the ratios between right and left ventricular weights and between right heart weight and bodyweight was also noted (Table 1).

Furthermore the test substance statistically significantly reduced the muscularisation of the distal pulmonary vessels of the rats (Table 2). This reduced pulmonary artery remodelling is equally a consequence of the statistically significant reduction of pulmonary hypertension.

TABLE 2

Effects of the substance used according to the invention (40 mg/kg/day for 14 days) on the muscularisation of distal pulmonary vessels of rats during 14 days' hypoxia in comparison with hypoxic control tests.

| Parameter | 14 days' hypoxia | |
|---|---|---|
| | Control n = 6 | Test substance n = 8 |
| Muscularised (%) | 76 ± 4 | 52 ± 5* |
| Partly muscularised (%) | 23 ± 4 | 39 ± 4* |
| Non-muscularised (%) | 1 ± 1 | 9 ± 3 |

* = significantly different in comparison with hypoxic control tests (p < 0.05)

In view of their effect described above, the compounds of formula I and their salts and biolabile esters are suitable as pharmaceutical compositions for larger mammals and humans for the treatment of hypertension, particularly for the treatment of certain forms of secondary hypertension. The compounds used according to the invention are particularly suitable for the treatment of those forms of secondary hypertension which may occur as a result of various non-cardiac diseases, preferably, for example, for the treatment of pulmonary hypertension of non-cardiac origin. The substances used according to the invention thereby offer an advantageous approach to the treatment and/or prevention of, in particular, hypoxia-related pulmonary hypertension and complications thereof, but without reducing normal systemic blood pressure.

For this purpose, dicarboxylic acids of formula I and their salts are used appropriately in pharmaceutical forms for parenteral, particularly i.v., administration, and mono- or diesters of formula I are used appropriately in orally administered pharmaceutical forms. The doses to be used can differ between individuals and naturally vary according to the nature of the condition to be treated, the substance used and the form of administration. For example, parenteral formulations will generally contain less active substance than oral preparations. However, pharmaceutical forms with an active substance content of 1 to 200 mg per individual dose are generally suitable for administration to larger mammals, particularly humans. The compounds of formula I, including their salts of acids and their biolabile esters, can be administered for this purpose in pharmaceutical compositions both for immediate and also delayed and/or controlled release of active substance.

The following examples are intended to illustrate the invention in further detail without restricting its scope in any way.

The following examples 1 and 2 describe pharmaceutical compositions useful in the method of the invention, which contain an active substance of formula I, and the production of such pharmaceutical compositions. The compounds of formula I used according to the invention can be produced for this purpose by the methods described in the previously mentioned U.S. Pat. No. 5,677,297, the entire disclosure of which is hereby incorporated herein by reference. Example 3 lists preferred compounds for use in the hypertension treatment method according to the invention.

EXAMPLE 1

Tablets containing (3S,2'R)-3-{1-[2'-(ethoxy-carbonyl)-4'-phenylbutyl]cyclopentane-1-carbonylamino}-2,3,4,5-tetrahydro-2-oxo-1H-1-benzazepine-1-acetic acid.

Tablets with the following composition per tablet were produced:

| | |
|---|---|
| (3S,2'R)-3-{1-[2'-(ethoxycarbonyl)-4'-phenyl-butyl]cyclopentane-1-carbonylamino}-2,3,4,5-tetrahydro-2-oxo-1H-1-benzazepine-1-acetic-acid | 20 mg |
| Maize starch | 60 mg |
| Lactose | 135 mg |
| Gelatin (as 10% solution) | 6 mg |

The active substance, the maize starch and the lactose were thickened with the 10% gelatin solution. The paste was comminuted and the resulting granules were placed on a suitable sheet and dried at 45° C. The dried granules were fed through a crushing machine and mixed with the following further adjuvants in a mixer:

| | |
|---|---|
| Talc | 5 mg |
| Magnesium stearate | 5 mg |
| Maize starch | 9 mg | and then compressed to form tablets of 240 mg.

EXAMPLE 2

Injection solution containing (3S,2'R)-3-[1-(2'-carboxy-4'-phenylbutyl)cyclopentane-1-carbonylamino]-2,3,4,5-tetrahydro-2-oxo-1H-1-benzazepine-1- acetic acid.

An injection solution with the following composition per 5 ml was produced:

| | |
|---|---|
| (3S,2'R)-3-[1-(2'-carboxy-4'-phenylbutyl)-cyclopentane-1-carbonylamino]-2,3,4,5-tetra-hydro-2-oxo-1H-1-benzazepine-1-acetic acid | 10 mg |
| $Na_2HPO_4.7H_2O$ | 43.24 mg |
| $NaH_2PO_4.2H_2O$ | 7.72 mg |
| NaCl | 30.0 mg |
| purified water | 4948.0 mg |

The solids were dissolved in water, the solution was sterilized and filled into ampoules in 5 ml portions.

EXAMPLE 3

Preferred embodiments of formula I for use according to the invention for the production of pharmaceutical compositions for the treatment of hypertension, particularly for the treatment of secondary forms of hypertension such as e.g. pulmonary hypertension, are for example (including the salts of acids):

3-{1-[2'-(ethoxycarbonyl)-4'-phenylbutyl]cyclopentane-1-carbonylamino}-2,3,4,5-tetrahydro-2-oxo-1H-1-benzazepine -1- acetic-acid-tert-butylester.

3-{1-[2'-(ethoxycarbonyl)-4'-phenylbutyl]cyclopentane-1-carbonylamino}-2,3,4,5-tetrahydro-2-oxo-1H-1-benzazepine-1-acetic-acid.

(3S,2'R)-3-{1-[2'-ethoxycarbonyl)-4'-phenylbutyl]-cyclopentane-1-carbonylamino}-2,3,4,5-tetrahydro-2-oxo-1H-1-benzazepine-1- acetic-acid-tert-butylester.

(3S,2'R)-3-{1-[2'-(ethoxycarbonyl)-4'-phenylbutyl]cyclopentane-1-carbonylamino}-2,3,4,5-tetrahydro-2-oxo-1H-1-benzazepine-1-acetic-acid.

(3S,2'R)-3-{1-[2'-(carboxy-4'-phenylbutyl]cyclopentane-1-carbonylamino}-2,3,4,5-tetrahydro-2-oxo-1H-1-benzazepine-1-acetic-acid.

3-{1-[2'-(tert-butoxycarbonyl)-4'-phenylbutyl]-cyclopentane-1-carbonylamino}-2,3,4,5-tetrahydro-2-oxo-1H-1-benzazepine-1-acetic-acid-tert-butylester.

3-[1-(2-carboxy-4'-phenylbutyl)cyclopentane-1-carbonylamino]-2,3,4,5-tetrahydro-2-oxo-1H-1-benzazepine-1-acetic-acid.

3-{1-[2'-(tert-butoxycarbonyl)-4'-phenylbutyl]cyclopentane-1-carbonylamino}-2,3,4,5-tetrahydro-2-oxo-1H-1-benzazepine-1-acetic-acid-benzylester.

3-[1-(2'-carboxy-4'-phenylbutyl)cyclopentane-1-carbonylamino]-2,3,4,5-tetrahydro-2-oxo-1H-1-benzazepine-1-acetic-acid-benzylester.

3-{1-[2'-(tert-butylcarbonyloxymethoxycarbonyl)-4'-phenylbutyl]cyclopentane-1-carbonylamino}-2,3,4,5-tetrahydro-2-oxo-1H-1-benzazepine-1-acetic-acid-benzylester.

3-{1-[2'-(pivaloyloxymethoxycarbonyl)-4'-phenylbutyl]cyclopentane-1-carbonylamino}-2,3,4,5-tetrahydro-2-oxo-1H-1-benzazepine-1-acetic-acid.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method of inhibiting secondary hypertension in a mammal, said method comprising administering to said mammal an effective secondary hypertension inhibiting amount of a compound corresponding to formula I:

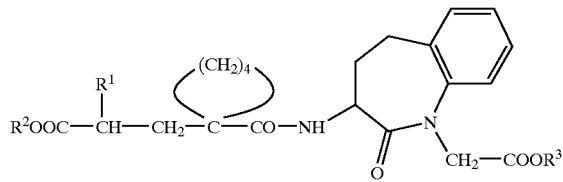

wherein
$R^1$ stands for a phenyl-lower-alkyl group which can optionally be substituted on the phenyl ring by lower alkyl, lower alkoxy or halogen;
or for a naphthyl-lower-alkyl group,
$R^2$ is hydrogen or a group forming a biolabile ester and
$R^3$ is hydrogen or a group forming a biolabile group, or a physiologically acceptable salt of an acid of formula I.

2. A method according to claim 1, wherein said mammal is a larger mammal or human suffering from secondary hypertension caused by a non-cardiac disease.

3. A method according to claim 2, wherein said secondary hypertension is pulmonary hypertension.

4. A method according to claim 1, wherein at least one of $R^2$ and $R^3$ represents a biolabile ester forming group.

5. A method according to claim 4, wherein said biolabile ester forming group is selected from the group consisting of lower alkyl groups, or a phenyl or phenyl-lower-alkyl group, optionally substituted in the phenyl ring by lower alkyl or by a lower alkylene chain bonded to two adjacent carbon atoms, or a dioxolanylmethyl group, optionally substituted in the dioxolane ring by lower alkyl, or a $C_2-C_6$-alkanoyloxymethyl group optionally substituted on the oxymethyl group by lower alkyl.

6. A method according to claim 5, wherein said biolabile ester forming group is a phenyl, benzyl or indanyl group, optionally substituted by lower alkyl or by a lower alkylene chain bonded to two adjacent carbon atoms, or a (2,2-dimethyl-1,3-dioxolane-4-yl)methyl group.

7. A method according to claim 5, wherein $R^2$ is a biolabile ester forming group, and $R^3$ is hydrogen.

8. A method according to claim 1, wherein said compound corresponding to formula I is (3S,2'R)-3-{1-[2'-(ethoxycarbonyl)-4'-phenylbutyl]-cyclopentane-1-carbonylamino}-2,3,4,5-tetrahydro-2-oxo-1H-1-benzazepine-1-acetic-acid or a physiologically acceptable salt thereof.

9. A method according to claim 1, wherein said compound corresponding to formula I is administered in a pharmaceutical dosage form further comprising at least one pharmaceutical carrier or adjuvant.

10. A method of treating secondary hypertension caused by a non-cardiac disease state in a human or large mammal, said method comprising administering to said human or large mammal an effective blood pressure-lowering amount of a compound corresponding to formula I:

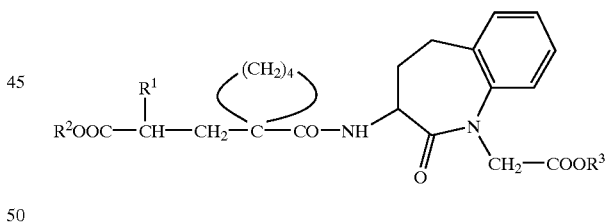

wherein
$R^1$ stands for a phenyl-lower-alkyl group which can optionally be substituted in the phenyl ring by lower alkyl, lower alkoxy or halogen;
or, $R^1$ is a naphthyl-lower-alkyl group,
$R^2$ is hydrogen or a group forming a biolabile ester and
$R^3$ is hydrogen or a group forming a biolabile group, or a physiologically acceptable salt of an acid of formula I, in a pharmaceutical dosage form further comprising at least one pharmaceutical carrier or adjuvant.

* * * * *